United States Patent
Guillot et al.

(10) Patent No.: US 9,239,404 B2
(45) Date of Patent: Jan. 19, 2016

(54) DEVICE AND METHOD FOR CONTINUOUS MONITORING OF PERSONS, VEHICLES, CONTAINERS OR PACKETS

(75) Inventors: Ludovic Guillot, Villemoisson/Orge (FR); Anne Reboli, Paris (FR); Dominique Abt, Antony (FR)

(73) Assignee: Commissariat a L'Energie Atomique et aux Energies Alternatives, Paris (FR)

(*) Notice: Subject to any disclaimer, the term of this patent is extended or adjusted under 35 U.S.C. 154(b) by 1039 days.

(21) Appl. No.: 12/992,263

(22) PCT Filed: May 11, 2009

(86) PCT No.: PCT/EP2009/055645
§ 371 (c)(1),
(2), (4) Date: May 9, 2011

(87) PCT Pub. No.: WO2009/138371
PCT Pub. Date: Nov. 19, 2009

(65) Prior Publication Data
US 2011/0205361 A1 Aug. 25, 2011

(30) Foreign Application Priority Data
May 13, 2008 (FR) ..................... 08 53081

(51) Int. Cl.
*G01T 1/16* (2006.01)
*G01V 5/00* (2006.01)
*G01T 1/167* (2006.01)

(52) U.S. Cl.
CPC .............. *G01V 5/0075* (2013.01); *G01T 1/167* (2013.01); *G01V 5/0083* (2013.01); *G01N 2223/626* (2013.01)

(58) Field of Classification Search
USPC ........................................................ 250/369
See application file for complete search history.

(56) References Cited

U.S. PATENT DOCUMENTS

| 7,265,353 | B2 * | 9/2007 | Evans | 250/366 |
| 2004/0113775 | A1 * | 6/2004 | Bohinc, Jr. | 340/539.26 |
| 2004/0178339 | A1 | 9/2004 | Gentile | |
| 2005/0023477 | A1 | 2/2005 | Archer | |
| 2007/0034808 | A1 | 2/2007 | Evans | |

OTHER PUBLICATIONS

International Preliminary Report on Patentability in International Application No. PCT/EP2009/055645, mailed Feb. 17, 2011.
Guillot, L., "Extraction of full absorption peaks in airborne gamma-spectrometry by filtering techniques coupled with a study of the derivatives. Comparison with the window method", Journal of Environmental Radioactivity, vol. 53, pp. 381-398 (2001).
Gutierrez, S. et al., "Contribution of a germanium detector in mobile gamma-ray spectrometry. Spectral analysis and performance", Nuclear Instruments & Methods in Physics Research, Section A, V. 482, pp. 425-433 (2002).
Perrin, J. et al., "Determination of the vertical distribution of radioelements (K. U, Th, Cs) in soils from portable HP-Ge spectrometer measurements: A tool for soil erosion studies", Appllied Radiation and Isotopes, vol. 64, pp. 830-843 (2006).
International Search Report, PCT/EP2009/055645, dated Sep. 8, 2009.
French Preliminary Examination Report, FR 0853081, dated Feb. 26, 2009.

* cited by examiner

*Primary Examiner* — David Porta
*Assistant Examiner* — Shun Lee
(74) *Attorney, Agent, or Firm* — Nixon Peabody LLP

(57) ABSTRACT

A device for continuously monitoring persons, vehicles, containers or packets comprising a device for detecting and identifying in real time a moving gamma radiation source.

16 Claims, 6 Drawing Sheets

Event history

| beacon serial no. | Data / time | beacon position | DETECT type alarm | Category | Radionuclide | IPA alarm type |
|---|---|---|---|---|---|---|
| 7019 | 11/02/2008 10:33:10 | 0 | Unlimely | Natural | k-40 | |
| 7019 | 11/02/2008 10:33:11 | 1 | Unlimely | Natural | k-40 | |
| 7019 | 11/02/2008 10:33:12 | 0 | Unlimely | Natural | k-40 | |
| 7019 | 11/02/2008 10:33:35 | 1 | Justified | Industrial | Co-60 | Threshold 1 |
| 7019 | 11/02/2008 10:33:36 | 0 | Justified | Industrial | Co-60 | Threshold 2 |
| 7019 | 11/02/2008 10:33:36 | 1 | Justified | Industrial | Co-60 | Threshold 2 |
| 7019 | 11/02/2008 10:33:37 | 0 | Justified | Industrial | Co-60 | Threshold 2 |
| 7019 | 11/02/2008 10:33:37 | 1 | Justified | Industrial | Co-60 | Threshold 2 |
| 7019 | 11/02/2008 10:33:38 | 0 | Justified | Industrial | Co-60 | Threshold 2 |
| 7019 | 11/02/2008 10:33:38 | 1 | Justified | Industrial | Co-60 | Threshold 2 |
| 7019 | 11/02/2008 10:33:39 | 0 | Justified | Industrial | Co-60 | Threshold 2 |
| 7019 | 11/02/2008 10:33:39 | 1 | Justified | Industrial | Co-60 | Threshold 2 |
| 7019 | 11/02/2008 10:33:42 | 0 | Justified | Industrial | Co-60 | Threshold 1 |

FIG. 6

DEVICE AND METHOD FOR CONTINUOUS MONITORING OF PERSONS, VEHICLES, CONTAINERS OR PACKETS

CROSS REFERENCE TO RELATED APPLICATIONS or PRIORITY CLAIM

This application is a National Phase of PCT/EP2009/055645, filed May 11, 2009, entitled, "DEVICE AND METHOD FOR CONTINUOUSLY CHECKING PEOPLE, VEHICLES, CONTAINERS OR PACKAGES", and claims priority of French Patent Application No. 09 53081, filed May 13, 2008.

TECHNICAL FIELD

The present invention relates to a device and method for continuously monitoring persons, vehicles, containers or packets comprising a device for detecting and identifying in real time a moving gamma radiation source.

The field of the invention is that of preventing risks related to illegal transports of radioactive and nuclear materials, and more particularly to that of continuous monitoring and without any compulsory slowing-down point for persons, vehicles, containers or packets.

STATE OF THE PRIOR ART

More than 300,000 authorized packets of radioactive materials (for example sources used in industry or in radiopharmaceutical products), without including the transports of materials containing strong concentration of natural radionuclides, circulate in France every year, via a terrestrial, maritime or air route. In this flow, detection of movements with a criminal purpose is sought by means of a radiological monitoring system.

Radiological monitoring of goods and individuals at the scale of a territory requires the use of suitable systems for detecting radioactivity in order not to perturb normal traffic nor unnecessarily worry the population. In particular, such systems should continuously monitor the flows of persons and goods without however limiting the movements thereof. These detection systems should therefore be able to detect a moving source, the speed of which may attain 100 km/h at distances of several meters.

In order to differentiate illegally transported radioactive sources from many other sources legally crossing the territory or at our frontiers, it is just as important to detect a radioactive source as to identify its nature. The identification of such a source should be accomplished rapidly, in real time and with a false alarm rate as low as possible. It is therefore necessary in order to limit the number of material transports to be inspected, to resort to a system allowing detection and immediate identification of the detected radionuclides.

In the field of detection and identification of moving radioactive sources, several devices are thereby known.

A first device of the known art, described in U.S. Patent Application Publication No. 2005/0023477, which is a modular and transportable detector, with which one or more rapidly moving radioactive sources may be detected and identified, comprises at least one radioactivity detector operating at room temperature, a digital spectrometer allowing sampling of the signal over the periods of less than 150 ms and an acquisition and processing unit. Detection and identification of radioactive anomalies are successively carried out by two algorithms. In a first phase, an algorithm based on the SPRT (Sequential Probability Ratio Test) method allows determination of whether the counting variations are due to statistical fluctuations of the radiological background or to a radioactive anomaly. Once the representative spectrum of a radioactive anomaly is isolated, a second algorithm allows identification of the source at the origin of the anomaly.

A second device of the known art, described in U.S. Patent Application Publication No. 2007/0034808, which is a fixed detector allowing detection and identification of one or more rapidly moving radioactive sources, comprises at least one radioactivity detector operating at room temperature, a digital spectrometer allowing sampling of the signal over periods at least equal to 125 ms and an acquisition and processing unit. The detection of a radioactive anomaly is first accomplished by correlation between several spectra which contain the information of the passage of a radioactive source, hence a necessarily short counting time. Once the anomaly is isolated, identification of the radionuclide is accomplished by matching the energy of the detected anomaly with the emission energy of the radionuclide contained in a library.

Further, a known algorithm for detecting and identifying gamma anomalies in a spectrum of the art, described in "Extraction of full absorption peaks in airborne gamma-spectrometry by filtering techniques coupled with a study of the derivatives. Comparison with the window method" by L. Guillot (Journal of Environmental Radioactivity, 53, 2001), which is an algorithm for detecting and identifying radionuclides by analyzing the spectral profile of the known art developed for analyzing airborne gamma measurements recorded from a sodium iodide (NaI) detector, is based on the localization of total absorption peaks, over the whole energy range from 0 to 3 MeV. This algorithm in spite of low counting statistics due to the short counting times (from 0.5 to 5 s), allows detection and identification of gamma anomalies on a single spectrum, without requiring prior knowledge of the present radionuclides.

The object of the invention, relatively to these devices of the known art, is to improve detection of moving radioactive sources and their identification in real time.

DISCUSSION OF THE INVENTION

The invention relates to a device for continuously monitoring persons, vehicles, containers or packets comprising a device for detecting and identifying in real time a moving gamma radiation source, comprising:

at least one radiation detector delivering a signal proportional to the gamma radiation, at least one spectrometer allowing sampling and shaping of this signal, an acquisition and processing unit allowing automatic processing of the data from the spectrometer, a remote monitoring station, characterized in that this acquisition and processing unit comprises means for analyzing the spectrum successively including:

means for smoothing this spectrum,
means for calculating a reference spectrum
means for subtracting this reference spectrum,
means for seeking the total absorption peaks,
first means for validation of the detection of the peaks,
means for estimating the background under the validated peaks of the spectrum,
means for calculating the characteristics of the peaks,
second means for validation of the detection of the peaks,
means for identifying the radionuclides of the radioactive source,
means for viewing the results.

In an alternative embodiment, at least one lead or copper screen is added on one of the faces of at least one detector. Said at least one spectrometer may be an analog spectrometer which allows sampling of the signal at least every second. This may also be a digital spectrometer which allows sampling of the signal at least every 0.5 seconds.

In an alternative embodiment, the detector comprises at least one sodium iodide crystal. When it comprises several crystals, the device of the invention comprises a spectrometer for each crystal and means for summing the resulting signals before they are sent to the acquisition and processing unit. Each crystal has a spectrometer in order to directly shape the signals at the output of the latter. If in a beacon, several crystals are present, the signals from each spectrometer are synchronized and then summed before processing by the algorithm. By increasing the number of crystals, it is possible to increase the sensitivity of the device by the increase in its surface area.

The device of the invention may further include:
a system for taking pictures,
a GPS positioning system,
a system for remote transmission of data to a remote monitoring station,
a neutron detector.

In an alternative embodiment, several devices according to the invention may also be connected together or connected to the same remote monitoring station, thereby forming a network. With this, it is possible to correlate the data from several devices and infer therefrom additional information on the displacement of a source carrier or on the specific localization of this source, for example.

The invention also relates to a method for continuously monitoring persons, vehicles, containers, or packets comprising detection and identification in real time of a moving gamma radiation source, comprising the following steps:
recording the spectrum of the radiation emitted by this source,
analyzing the spectrum of the detected signal, characterized in that this analysis step comprises the following phases:
smoothing this spectrum,
calculating a reference spectrum,
subtraction of this reference spectrum,
search for the total absorption peaks,
first validation of the detection of the peaks,
estimating the background under the validated peaks of the spectrum,
calculating the characteristics of the peaks,
second validation of the detection of the peaks,
identification of the radionuclides of the radioactive source,
viewing the results, by classifying a detected source as not being a threat, as possibly being a threat or as being a threat.

Advantageously, the smoothing phase comprises fitting of a polynomial of degree 4 onto the raw data by the method of least squares. The reference spectrum is an average spectrum calculated on a parameterizable number N of measurements (N is a positive integer greater than 1). The reference spectrum is recalculated periodically from the last N measurements. The calculation of the reference spectrum does not take into account a measurement point for which at least one peak has been detected, validated and identified as resulting from the emission of a radionuclide. The phase for seeking peaks comprises the successive study of first and second derivatives of the spectrum, a peak being detected every time the first derivative assumes positive values or the second derivative assumes negative values. In the first validation of the detection of the peaks, a peak is validated when the first and second derivatives exceed a respective threshold. In the second validation of the detection of the peaks, a peak is validated if the calculated area of this peak is greater than the associated decision threshold and if the resolution of this peak is greater than half the theoretical resolution. In the phase for identifying radionuclides of the source, the energies of the detected and validated total absorption peaks are compared with the energies given by a table of radioelements defined by the user.

Advantageously, the invention relates to a real-time device and method (at a rate of one second) for detecting and identifying radioactive sources present on a moving carrier (persons, vehicle, packet, container) and not an acquisition but an analysis of data a posteriori, with which an area may be mapped and the presence and amount of radioactive elements may be identified.

Advantageously, the claimed invention relates to a device and a method allowing an alarm to be delivered in real time following the identification of an illicit radioactive source while excluding false alarms due to natural radioactive sources or used in medical diagnosis or care.

In the invention, a remote station is used for validating the alarm and allowing an operator to identify in real time the carrier (directly or upon observing the video triggered by the alarm). For this, the relevant data (spectrum, result of the identification, level of the energy peak, pictures taken during the emission of the alarm) and the alarm are sent in real time to the remote monitoring station.

In the invention, the transmitted alarms are parameterizable depending on the level or risk.

From the point of view of the treatment required for this real-time detection and identification, the originality of the invention is based on a method for searching peaks with a Gaussian shape in a spectral profile for acquisition times of the order of one second.

The taking into account of the background noise is original in the sense that in the invention, it is accomplished in a sliding way during the course of time, in order to take into account possible time changes in this background noise. The calculation of the reference spectrum also excludes any spectrum in which a radiological anomaly is detected. The reference spectrum is thus representative of the local background noise of the site at a given instant.

As compared with the devices of the prior art previously analyzed and described in the aforementioned references, the method of the invention has the following advantages.

U.S. Patent Application Publication Nos. 2005/0023477 and 2007/0034808 refer to methods for analyzing a signal in real time. However, the proposed radionuclide detection algorithms are based on statistical methods. The radionuclide detection method proposed within the scope of the invention is, as for it, based on a method for analyzing the spectral profile, which has the advantage of being able to operate without any assumption on the number and on the nature of the radioelements to be detected. Moreover, this type of processing allows better estimation of the energy of a total absorption peak and therefore facilitates its identification.

The referenced document "Extraction of full absorption peaks in airborne gamma-spectrometry by filtering techniques coupled with a study of the derivatives. Comparison with the window method" by L. Guillot (Journal of Environmental Radioactivity, 53, 2001) refers to a method for processing the signal based on the analysis of the spectral profile. This algorithm allows detection of very small amounts of radionuclides but it was specifically developed within the scope of airborne radiological monitoring and operates without any information on the ambient radiological background. The method for detecting radionuclides proposed within the scope of the invention takes into account the ambient radiological background and its change over time thereby allowing improvement in its detection performances.

SHORT DESCRIPTION OF THE DRAWINGS

FIG. 6 illustrates the viewing of the results.

DETAILED DISCUSSION OF PARTICULAR EMBODIMENTS

Figure 1:
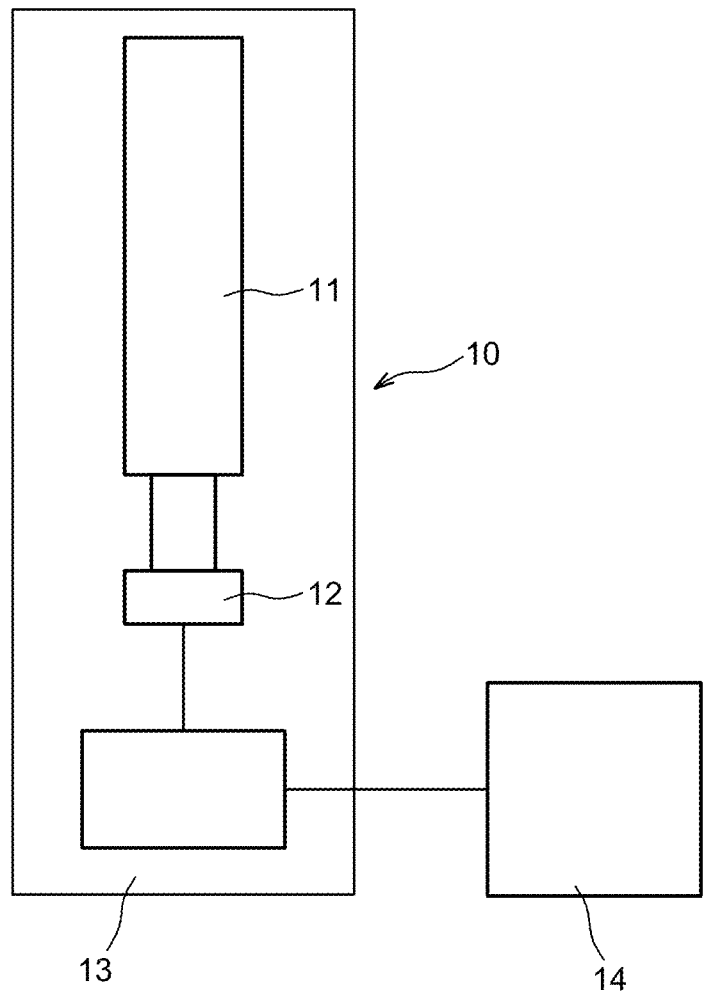
FIG. 1 illustrates the device of the invention.

As illustrated in FIG. 1, the device of the invention 10, in order to cover the needs relative to the detection and identification of moving gamma radiation sources comprises:
 at least one detector 11,
 at least one analog or digital spectrometer 12,
 an acquisition and processing unit 13,
 a monitoring station 14.

The originality of the invention is mainly based on a specific method for analyzing spectra operating on the acquisition and processing unit and allowing real-time detection and identification of radionuclides of the radioactive source.

1. Said at Least One Detector 11

Said at least one detector 11 for example comprises one or more sodium iodide (NaI) crystals selected for their large detection volume (unit size 10.16 cm×10.16 cm×40.64 cm). This detection volume provides significant detection efficiency, required for measurements carried out over very short times. Further, with such crystals it is possible to obtain spectroscopic information of a radioactive signal allowing its identification.

A screen may also be added on one or several faces of the detector, in order to allow a reduction in the radiological background and therefore an improvement of detection in a given direction. This screen may consist of a lead sheet with a thickness of 1 to 2 mm and of a copper sheet with a thickness of 0.5 mm.

2. Said at Least One Spectrometer 12

The detected signal is recovered at the output of the detector 11 by an analog or digital spectrometer 12. The latter allows sampling of the signal, at least every second for an analog spectrometer and every 0.5 second at least for a digital spectrometer.

If several NaI crystals are used for the detection, a spectrometer is used for each crystal and the resulting signals are summed before they are sent to the acquisition and processing unit 13.

This spectrometer 12 allows sampling of the signal from an NaI detector; the sampling period being greater than 0.5 s.

3. The Acquisition and Processing Unit 13

The sampled signal is transmitted to the acquisition and processing unit 13 consisting of different input and output interfaces, of a processor, and of a data storage unit and controlled by an operating system. The acquisition and processing unit 13 executes the different steps of the method of the invention allowing analysis of the data.

The acquisition and processing unit 13 allows acquisition of the signal, operation of detection and identification algorithms, and optionally the transfer of information relating to an anomaly detection towards a remote fixed control station 14. The acquisition and processing unit 13 consists of a processor, of a data storage unit, such as for example a hard disk.

In an exemplary embodiment of the device for detecting and identifying moving gamma sources, the latter uses commercially available electronic components and a radioactive anomaly detection and identification algorithm specifically developed for the application.

The gamma spectra recorded by the acquisition processing unit 13 are formed by the sum of a continuous radiological background and of one or several total absorption peaks which are the characteristic spectral contributions of the present radioelements. Radiation diffusion, gamma background noise of the instrumentation as well as cosmic radiations are the main contributions to the continuous radiological background.

The detection and identification of the radioelements are carried out from the total absorption peak(s) thereof present on a spectrum. The processing of the measurements allows these total absorption peaks to be isolated from the radiological background by a method for analyzing this spectral profile and the emitter thereof may then be identified.

For this, the method of the invention solves several difficulties:

The acquisition time, necessarily short in order to obtain good sensitivity to fast moving sources, causes significant statistical fluctuations of the gamma spectrum. The amplitude of these fluctuations may be greater than the amplitude of the total absorption peaks.

The resolution of the NaI type detector is of the order of about 8% at 662 keV. It contributes to reducing the peak-over-radiological-background ratio in each channel and makes the detection and localization of the peaks all the more difficult.

The radioelements ($^{40}$K, $^{238}$U and $^{232}$Th and their daughter products) naturally present on the whole of the globe generate peaks and a radiological background which may interfere with the detection and localization of the peaks of interest.

The method of the invention allowing detection and identification of moving radioactive sources is described in detail hereafter. The search for total absorption peaks is carried out independently for each spectrum. The processing algorithm is based on a method for analyzing the spectral profile allowing isolation of one or more radioactive anomalies in a spectrum.

Figure 2:
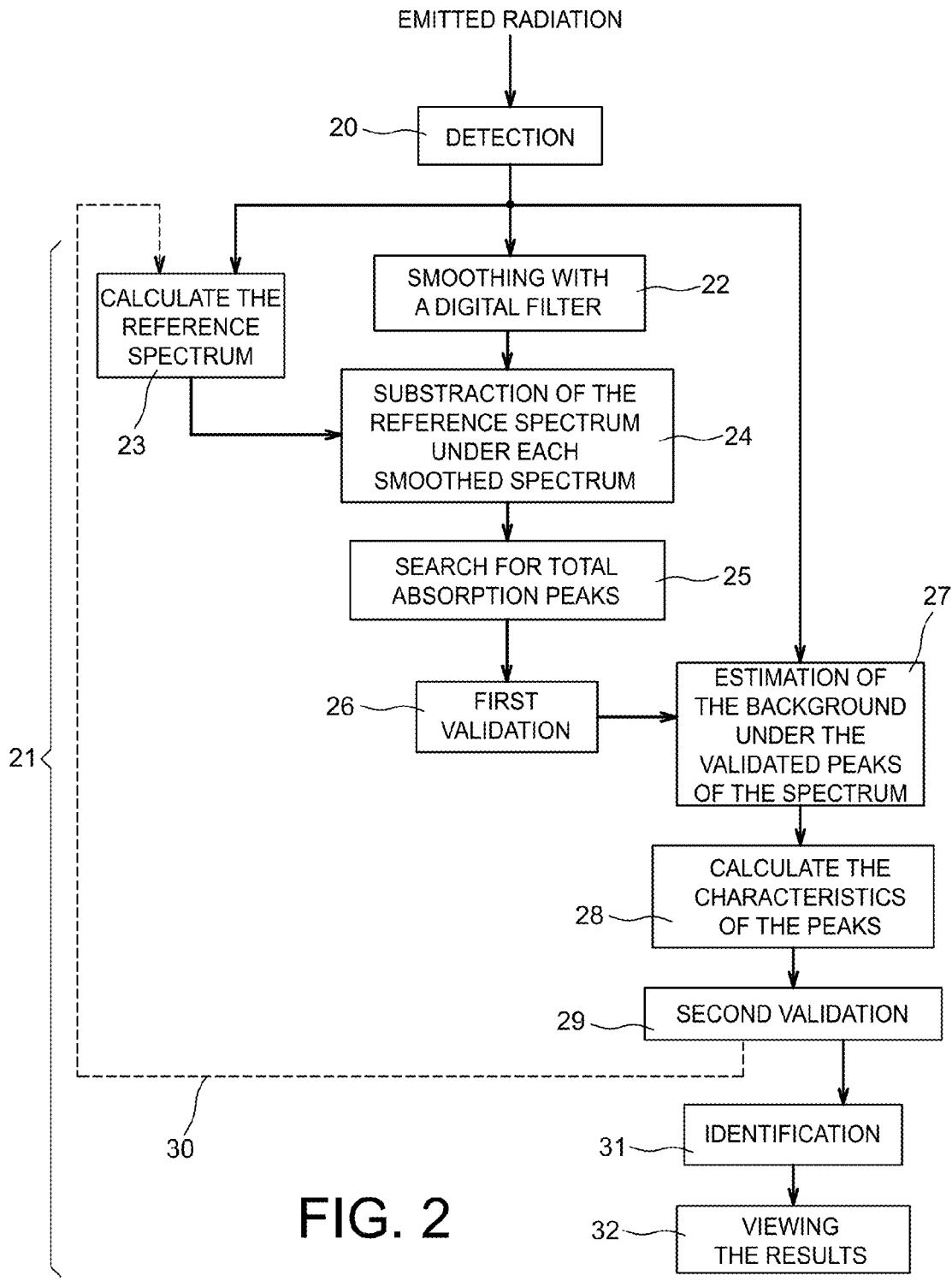
FIG. 2 illustrates the different steps of the method of the invention.

As illustrated in FIG. 2, the method of the invention after a step for detecting the signal 20, comprises a step for analyzing the spectrum of this signal 21 including the following phases:

1. Smoothing of the Raw Spectrum 22:

Because of the strong statistical fluctuations of the raw spectrum and of the low amplitude of the total absorption peaks relatively to the radiological background, a step for smoothing the raw spectrum is required. The smoothing phase is based on fitting a polynomial of degree 4 on the raw data by the method of least squares. The number of points, on which the polynomial is fitted, varies depending on the energy. This smoothing phase allows elimination of the non significant fluctuations of the raw spectrum before other processing operations.

Figure 3:
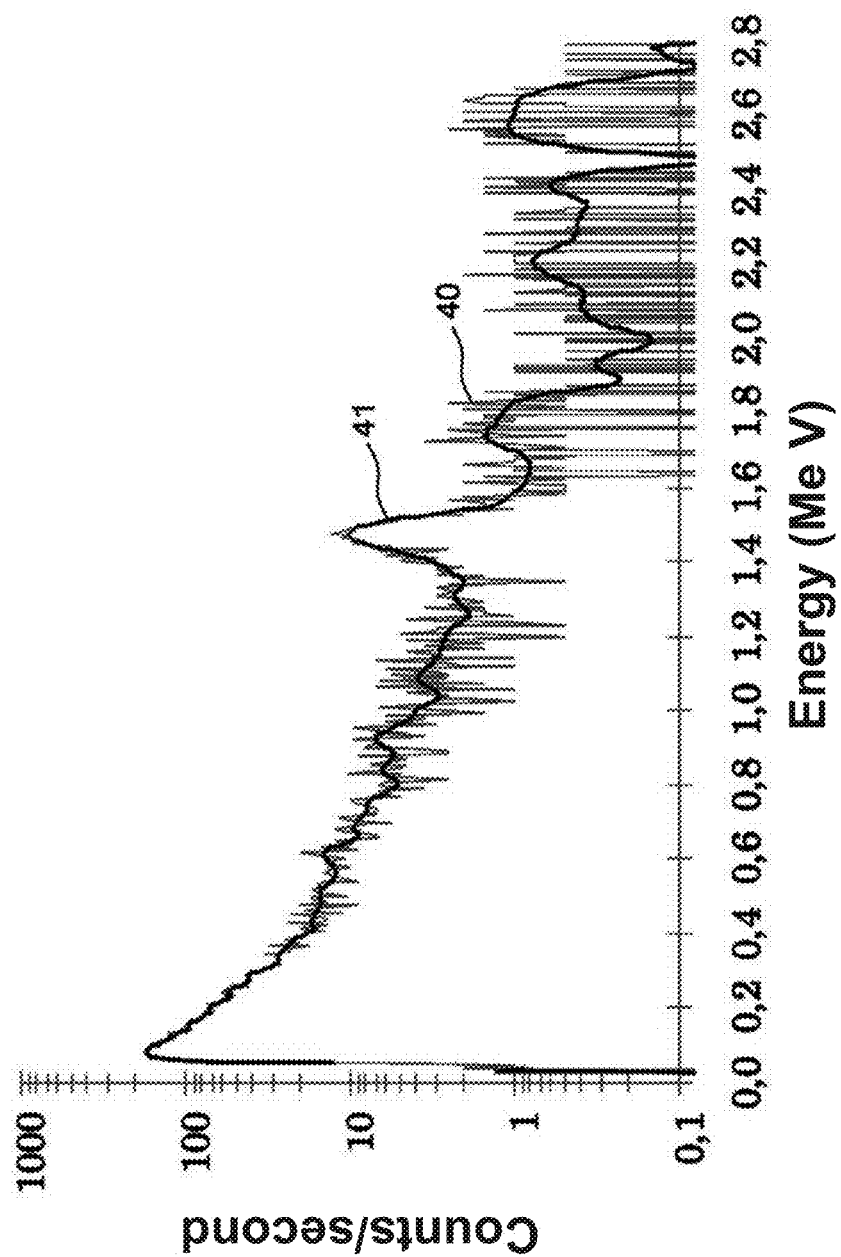
FIG. 3 illustrates the smoothing of a raw spectrum with a digital filter.

FIG. 3 illustrates this phase for smoothing a raw spectrum 40 with a digital filter in order to obtain a filtered spectrum 41.

2. Calculating a Reference Spectrum 23:

In order to take into account the natural radioactivity of the site, a reference spectrum representing the contributions of the continuous radiological background and of the surrounding radionuclides is evaluated. This reference spectrum is the average spectrum calculated on a parameterizable number N of measurements. In order to take into account possible variations in surrounding radioactivity, the reference spectrum is recalculated periodically, from the last N measurements.

The calculated reference spectrum, which should represent the ambient radioactivity of the site, should not include measurements made in the presence of anomalies. The method of the invention gives the possibility of not taking into account in the calculation of the reference spectrum, a measurement point for which one or several peaks have been detected, validated and identified as resulting from the emission of one of the sought radionuclides.

3. Subtraction of this Reference Spectrum 24:

The most recent reference spectrum is subtracted from the smoothed spectra.

4. Searching for the Peaks 25:

The search for total absorption peaks is carried out by studying the first and second derivatives of this spectrum. Both derivatives are successively calculated on each spectrum. A peak is detected every time that the first derivative assumes positive values or the second derivative assumes negative values.

Figure 4:
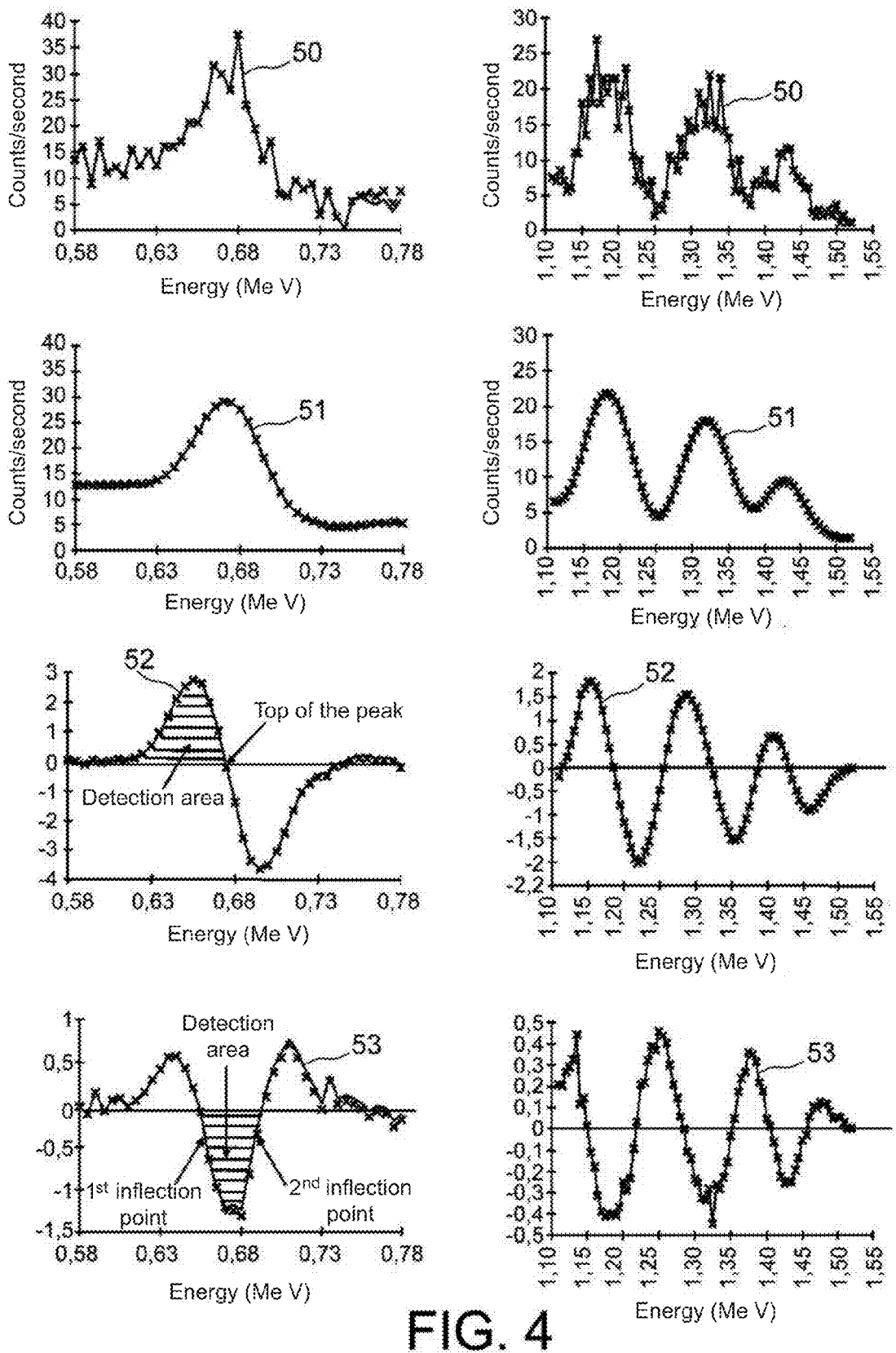
FIG. 4 illustrates the search for total absorption peaks by studying the first and second derivatives of the spectrum after filtering.

The curves of FIG. 4 illustrate this phase for searching for total absorption peaks by the study of the first and second derivatives of the spectrum after filtering. In this FIG. 4, are thus illustrated:

the raw spectrum 50,
the filtered spectrum 51,
the first derivative 52,
the second derivative 53.

5. First Validation of the Detection of the Peaks 26

A first validation phase for the detection of the peaks is added in order to reject non significant fluctuations. For this, a sensitivity threshold is determined experimentally for each derivative with which it is possible to evaluate the significance of the relevant peak. A peak is validated when both derivatives exceed a respective threshold.

6. Estimation of the Radiological Background Under the Non-Smoothed Spectra 27:

The characteristics of the total absorption peaks validated during the previous phase are calculated from the raw spectra. Once the spectral regions including one or several peaks are localized, the radiological background under the peak(s) is estimated and then subtracted.

Figure 5:
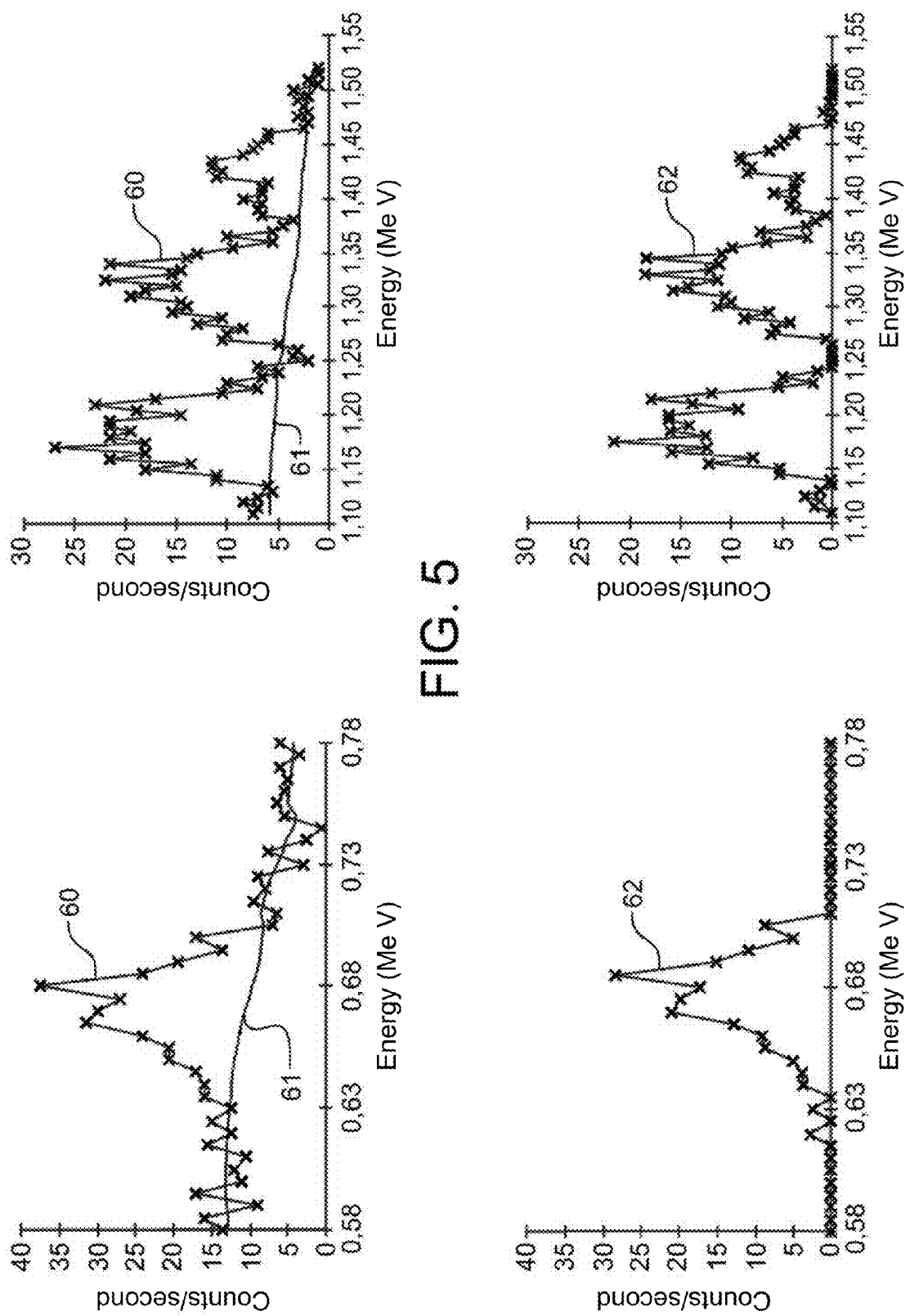
FIG. 5 illustrates the estimation of the radiological background under non-smoothed spectra.

The curves of FIG. 5 illustrate this phase for estimating the radiological background under non-smoothed spectra. In this FIG. 5, are thus illustrated:

the raw spectrum 60,
the adjusted continuous background 61,
the absorption peaks 62.

7. Calculating the Characteristics of the Peaks 28:

By assuming that the absorption peaks are properly modeled by a Gaussian profile, the area of the peaks, their resolution and the associated decision threshold may be calculated.

8. Second Validation of the Detection of the Peaks 29:

A second validation of the detection of the peaks is carried out. If the calculated area of a peak is greater than an associated decision threshold and if the resolution of this peak is greater than half the theoretical resolution, then the detection of this peak is validated. Only validated peaks are retained.

When one or several peaks have been detected and validated in a spectrum, this spectrum is not taken into account in the calculation of the reference spectrum (link 30).

9. Identification of the Detected Radionuclides 31:

The energies of the detected total absorption peaks validated during previous phases are compared with the energies given by a table of radioelements defined by the user, thereby allowing automatic identification of the detected radionuclides.

The radionuclides to be identified are distributed in four categories: natural, medical, industrial and nuclear. Depending on the category, it is possible to determine whether the detected radionuclide(s) represent a potential threat and whether it is necessary to trigger an alarm.

10. Viewing the Results 32:

With the method of the invention it is possible to classify each event in one of three categories with which it is possible to evaluate the dangerousness of the detected source:

a. The detected source is not a threat.
b. The detected source may be a threat.
c. The detected source is a threat.

FIG. 6 illustrates this phase for viewing the results. The result of this analysis may be simply viewed on the remote fixed station: a color may be associated with each event category: red (area 70) indicates that the detected source is a threat, orange indicates a possible threat while green (area 71) indicates that there is no detection or that the detected source is not threatening.

If the result obtained by this data processing method is the detection of an illegal transport of radioactive materials, alarms may then be triggered, notably a visual indication on a screen or the transmission of the results to a remote fixed station or further the triggering of recording of the taken pictures.

Alternative Embodiments of the Device of the Invention

Many alternatives of the device of the invention are possible without departing from the scope of the invention.

In particular, the sodium iodide (NaI) detector may be replaced with other scintillator materials, such as for example a lanthanum bromide ($LaBr_3$) or lanthanum chloride ($LaCl_3$) detector. Although of a smaller size, these detectors nevertheless have the advantage of having a smaller energy resolution allowing more easy identification of an anomaly on a spectrum. On the other hand, these detectors are not yet available in large volumes at competitive prices.

In an alternative embodiment, several devices according to the invention may be connected together or connected to a same local or remote monitoring station, thereby forming a network of at least two stations. The networking of several devices according to the invention then allows correlation of the data from the devices and additional information may be inferred therefrom on the position or the speed of the moving radioactive source.

For example, the correlation of signals from two devices placed on the same side relatively to the moving source (along a road for example) allows i.a. information to be obtained on the direction of displacement of the source.

Another alternative embodiment uses two devices located on either side of the moving source (for example, monitoring vehicles at the frontiers). With this configuration it is possible to obtain i.a. information on the activity of the source and on the relative distance to each point of the measurement device.

The use of three devices or more allows monitoring of a entire area (such as for example a car park or a railway station hall or of prefecture offices). With the correlation of the signals from the devices it is possible to add a localization of this source to the estimation of the activity of the source.

The device of the invention may further comprise a system for taking pictures, such as for example a camera. In a first phase, this picture-taking system may transmit information to the device such as the distance and the transit speed of a radioactive object thereby allowing refinement of the diagnosis on the dangerousness of the source. In a second phase, the triggering of this system may be conditioned by the detection and identification of a source estimated as being potentially dangerous. The thereby obtained pictures facilitate visual identification of the danger.

Also, the device of the invention may comprise a positioning system, such as a GPS (<<Global Positioning System>>) system, with which it is possible to absolutely date to within one millisecond and to localize to within one meter the device within a network of devices. This dating and localization information may be transmitted to a local or remote fixed station at the same time as radiological data thereby allowing identification without any ambiguity of the spectra and the alarms by their date and the localization of the device.

A remote data transmission system (GPRS, Wi-Fi, . . . ) may be added to the device of the invention. In this way, a detector which may operate in a standalone way is made available: the device of the invention may then operate continuously and transmit its results, regardless of its location of implantation, to a remote fixed monitoring station.

Several devices according to the invention may also be connected to the same remote fixed monitoring station thereby forming a network. With this, it is possible to correlate the data from several devices and to infer therefrom additional information on the displacement of a source carrier or on the specific localization of this source, for example.

The device of the invention may further comprise in addition to the gamma radiation detector, a neutron detector. Indeed, certain nuclear materials mainly emit neutrons either combined or not with gamma radiation emission. The measurements obtained by the combination of both detectors therefore allow monitoring of a larger number of radionuclides.

The invention claimed is:

1. A device for conducting continuous radiological and nuclear monitoring of a flow of persons, vehicles, containers or packets to thereby prevent risks related to illegal transport of radioactive and nuclear materials, and to detect and identify, at a site in real time, without any compulsory slowing-down point, a gamma radiation source present on a moving carrier, said device comprising:
   at least one radiation detector comprising at least one sodium iodide crystal selected for its detection volume, said at least one radiation detector operable to deliver a signal proportional to detected gamma radiation,
   at least one spectrometer coupled to the at least one radiation detector and operable to sample and shape the delivered proportional signal and generate a raw spectrum therefrom,
   an acquisition and processing unit coupled to the at least one spectrometer and including a processor operable to analyse the raw spectrum from the at least one spectrometer automatically and in real time,
   a system for taking pictures coupled to the acquisition and processing unit, and
   a link for transmitting analysis results from the acquisition and processing unit to a remote monitoring station,
   wherein said analysing by the processor includes:
   smoothing the raw spectrum to obtain a filtered spectrum,
   calculating a reference spectrum representing ambient radioactivity in the form of local background noise of the site,
   subtracting the reference spectrum from the filtered spectrum, searching for total absorption peaks in the subtracted and filtered spectrum, and performing a first validation of the detection of the total absorption peaks,
   estimating and subtracting the background under the validated total absorption peaks of the raw spectrum, calculating the characteristics of the total absorption peaks in the background subtracted raw spectrum and performing a second validation of the detection of the total absorption peaks,
   comparing energies of the detected and validated total absorption peaks with energies given in a table of radionuclides to thereby identify radionuclides of the gamma radiation source,
   categorizing the identified radionuclides in order to determine whether the gamma radiation source is a threat, and
   if the gamma radiation source is determined to be a threat:
   automatically triggering an alarm in real time, while excluding alarms due to natural radioactive sources or used in medical diagnosis or care,
   automatically triggering the system for taking pictures of the carrier of the gamma radiation source in order to identify it, and
   displaying the results, including the raw spectrum of the gamma radiation source, for examination by an operator.

2. The device according to claim 1, further comprising at least one lead or copper screen on one face of the at least one radiation detector.

3. The device according to claim 1, wherein said at least one spectrometer is an analog spectrometer for sampling the delivered proportional signal at least every second.

4. The device according to claim 1, wherein said at least one spectrometer is a digital spectrometer for sampling of the delivered proportional signal at least every 0.5 seconds.

5. The device according to claim 1, wherein the number of spectrometers is more than one, each spectrometer being associated with a corresponding crystal, the device further comprising processing devices for summing signals from each spectrometer before delivery to the acquisition and processing unit.

6. The device according to claim 1, further comprising a GPS positioning system to localize the device within a network of devices.

7. The device according to claim 1, further comprising a neutron detector coupled to the acquisition and processing unit and operable to detect sources emitting neutron.

8. A method for conducting continuous radiological and nuclear monitoring of a flow of persons, vehicles, containers or packets to thereby prevent risks related to illegal transport of radioactive and nuclear materials, and to detect and identify, at a site in real time, without any compulsory slowing-down point, a gamma radiation source present on a moving carrier, the method comprising:
   delivering a signal proportional to radiation emitted by the gamma radiation source, by using at least one radiation detector comprising at least one sodium iodide crystal selected for its detection volume, sampling, shaping said signal and generating a raw spectrum therefrom,
   analyzing the raw spectrum automatically and in real time, said analyzing including:
   smoothing the raw spectrum to obtain a filtered spectrum,
   calculating a reference spectrum representing ambient radioactivity in the form of local background noise of the site,
   subtracting the reference spectrum from the filtered spectrum, searching for total absorption peaks in the subtracted and filtered spectrum, and performing a first validation of the detection of the total absorption, estimating and subtracting the background under the validated total absorption peaks of the raw spectrum, calculating the characteristics of the total absorption peaks in the background subtracted raw spectrum, and performing a second validation of the detection of the total absorption peaks, identifying radionuclides of the gamma radiation source by comparing the energies of the detected and validated total absorption peaks with energies given in a table of radionuclides, categorizing the identified radionuclides in order to determine whether the gamma radiation source is a threat, if the gamma radiation source is determined to be a threat:
automatically triggering an alarm in real time, while excluding false alarms due to natural radioactive sources or used in medical diagnosis or care,
automatically triggering a system for taking pictures of a carrier of the gamma radiation in order to identify it,
displaying the results, including the raw spectrum of the gamma radiation source, origin of the alarm, for examination by an operator.

9. The method according to claim 8, wherein said smoothing comprises fitting a polynomial of degree 4 on the raw data by the method of least squares.

10. The method according to claim 8, wherein the reference spectrum is an average spectrum calculated on a parameterizable number N of measurements, N being a positive integer greater than 1.

11. The method according to claim 8, wherein the reference spectrum is recalculated periodically from N measurements.

12. The method according to claim 8, wherein the calculating of a reference spectrum does not take into account a measurement point for which at least one total absorption peak has been detected, validated and identified as resulting from the emission of radionuclide.

13. The method according to claim 8, wherein the searching for total absorption peaks comprises the successive study of the first and second derivatives of the subtracted and filtered spectrum, a total absorption peak being detected every time when the first derivative assumes positive values or the second derivative assumes negative values.

14. The method according to claim 13, wherein, in the first validation of the detection of the total absorption peaks, a total absorption peak is validated when the first and second derivatives exceed a respective threshold.

15. The method according to claim 8, wherein, in the second validation of the detection of the total absorption peaks, a total absorption peak is validated, if the calculated area of a total absorption peak is greater than an associated decision threshold and if the resolution of this total absorption peak is greater than half the theoretical resolution.

16. The method according to claim 8, wherein, in the identification, the energies of the detected and validated total absorption peaks are compared with the energies given by a table of radioelements defined by a user.

* * * * *